(12) United States Patent
Longoni et al.

(10) Patent No.: US 8,100,261 B2
(45) Date of Patent: Jan. 24, 2012

(54) DENTAL FLOSS PACKAGE

(75) Inventors: Paolo Longoni, Milan (IT); Ciro Lai, Trieste (IT); Elena Longoni, Trieste (IT)

(73) Assignee: Profimed S.r.l, Cassina de' Pecchi (Milan) (IT)

( * ) Notice: Subject to any disclaimer, the term of this patent is extended or adjusted under 35 U.S.C. 154(b) by 0 days.

(21) Appl. No.: 12/922,942

(22) PCT Filed: Dec. 29, 2009

(86) PCT No.: PCT/IB2009/055978
§ 371 (c)(1),
(2), (4) Date: Sep. 16, 2010

(87) PCT Pub. No.: WO2010/082103
PCT Pub. Date: Jul. 22, 2010

(65) Prior Publication Data
US 2011/0041869 A1 Feb. 24, 2011

(30) Foreign Application Priority Data
Jan. 19, 2009 (IT) .............................. MI2009A0043

(51) Int. Cl.
*A61C 15/04* (2006.01)
(52) U.S. Cl. ........ 206/397; 206/63.5; 206/470; 206/806
(58) Field of Classification Search .................. 206/389, 206/397, 398, 408, 409, 461, 467, 470, 471, 206/63.5, 806; 132/324
See application file for complete search history.

(56) References Cited

U.S. PATENT DOCUMENTS

| 3,512,634 | A |   | 5/1970  | Burch, Jr |
|-----------|---|---|---------|-----------|
| 4,706,843 | A | * | 11/1987 | Thornton ......................... 221/48 |
| 5,037,000 | A | * | 8/1991  | Selame .......................... 221/303 |
| 5,076,423 | A | * | 12/1991 | Russack ....................... 206/63.5 |
| 5,190,200 | A |   | 3/1993  | Hammerlund |
| 5,806,666 | A | * | 9/1998  | Chiang et al. ............... 206/63.5 |
| 5,913,418 | A |   | 6/1999  | Singh |
| 6,053,321 | A | * | 4/2000  | Kayser .......................... 206/470 |
| 6,129,090 | A |   | 10/2000 | Pillar |

(Continued)

FOREIGN PATENT DOCUMENTS
EP        0666224 A1    8/1995

(Continued)

OTHER PUBLICATIONS

International Search Report, dated Jul. 5, 2010, from corresponding PCT application.

*Primary Examiner* — Jacob K Ackun
(74) *Attorney, Agent, or Firm* — Young & Thompson (57) ABSTRACT

A dental floss package includes a box-shaped body, wherein the dental floss can be housed in the form of a spool, a cutting blade and a closing body, as well as an additional body (3, 23) provided with an aperture (3c) for the fastening thereof to a display. The additional body is obtained integrally with the box-shaped body or the closing body but is detachable along a weakening line (6). The box-shaped body (1, 11, 21, 110) and the closing body (2, 12, 22, 120) are also obtained integrally and joined along a thin folding line (5), and the box-shaped body (1, 11, 21, 110) is interference-coupled with the closing body (2, 12, 22, 120) by way of a wall encircling the spool (4).

21 Claims, 6 Drawing Sheets

U.S. PATENT DOCUMENTS

| | | |
|---|---|---|
| 6,302,121 B1 | 10/2001 | McConnell |
| 6,321,944 B1 * | 11/2001 | Cetrangolo .................. 222/105 |
| 6,715,603 B1 * | 4/2004 | Uribe .......................... 206/63.5 |
| 2003/0029472 A1 | 2/2003 | Adler |
| 2005/0000538 A1 | 1/2005 | Blasi et al. |
| 2005/0252807 A1 * | 11/2005 | Bott et al. .................... 206/389 |
| 2006/0196909 A1 | 9/2006 | Hadtke et al. |
| 2010/0269850 A1 * | 10/2010 | Souza ........................... 132/324 |

FOREIGN PATENT DOCUMENTS

| | | |
|---|---|---|
| WO | 0105665 A2 | 1/2001 |

* cited by examiner

DENTAL FLOSS PACKAGE

FIELD OF THE INVENTION

The present invention concerns a package for dental floss which has innovative features, both in terms of simplification and in terms of efficiency in the commercial supply chain.

BACKGROUND ART

So-called "dental floss" is well-known, the use of which is recommended by all dental technicians to their patients.

At the moment, one of the ways in which dental floss is made available to the public is spinning it around a spool, said spool being arranged in a small box provided with unwinding and cutting means. More precisely, the box is provided with a window, on an edge of which a small blade is applied, slightly raised at one end. In the ready-to-use package, the end of the dental floss coming out of the spool is caused to run through the window and is normally retained between the window edge and the blade; when a portion of floss must be used, it is pulled at said end, until the desired length is extracted, and then it is cut off causing it to rest on the cutting edge of the blade.

An original dental floss dispenser box is the one disclosed in Community Design registration no. 161815 in the name of the same Applicant.

Such a box normally consists of one or two components, which must be mutually mounted or coupled, for example in the form of housing and cover. This provides to manufacture two separate pieces and then to join them together, after having placed the floss spool between them. As can be guessed, this requires handling resources which are often dealt with by employing labour force.

US-A1-2003029472 discloses another type of container, wherein the two box components are hinged along a side edge, so as to allow the exit of an applicator from the upper surface.

These types of container are conceived as true complex applicators, suitable to last a long time to use a plurality of dental floss spools, which are gradually replaced when they are used up.

These types of containers are normally packaged and enclosed in a typical blister pack before they can be displayed for sale.

Consequently, there are additional packaging costs and a greater environmental impact due to package disposal.

The prior art offers also other types of disposable packages, simpler and more economical, which are suitable also for sales display but have other drawbacks. Some of such containers are disclosed in U.S. Pat. No. 3,512,634, U.S. Pat. No. 5,913,418 and EP-A1-0666224. These containers generally consist of a shaped portion of clear plastic material which acts as spool housing, coupled with a planar cardboard closing the package. These devices provide the use of material of different nature (plastics and cardboard) mutually coupled with adhesives, which implies the use of a gluing/joining station, as well as causing disposal problems.

SUMMARY OF THE INVENTION

The problem on which the invention is based is that of supplying a package and dispensing structure for dental floss which overcomes the mentioned drawbacks and which allows both to reduce manufacturing and packaging costs, and a smaller environmental impact.

This object is achieved through the features mentioned in the attached claims.

In particular, according to a first aspect of the invention, a dental floss package is provided, of the type comprising a box-shaped body, wherein the dental floss can be housed in the shape of a spool, further comprising a cutting blade and a closing body, as well as an additional body provided with an aperture for the fastening thereof to a display, wherein the additional body is obtained integrally with the box-shaped body or the closing body but is detachable along a weakening line, the box-shaped body and the closing body are also obtained integrally and are joined along a thin folding line, and wherein the box-shaped body is interference-coupled with the closing body by means of a wall encircling the spool.

According to another aspect, a dental floss package is provided, of the type comprising a box-shaped body obtained by moulding, wherein the dental floss can be housed in the shape of a spool, further comprising a cutting blade and a closing body, wherein the box-shaped body and the closing body are obtained integrally and are joined along a thin folding line, an additional body provided with an aperture for the fastening thereof to a display being further provided, and wherein the box-shaped body is interference-coupled with the closing body by means of a wall encircling the spool.

According to an original aspect, the closing body, turned upside down by 180° about the thin folding line, can be interference-coupled with the box-shaped body to form a dust-proof housing containing the dental floss spool.

According to another aspect, the box-shaped body and the closing body substantially consist of a planar plate wherefrom ribbings and perimetral walls project perpendicularly, apt to interference-couple one with the other to form a housing.

According to a further aspect, such ribbing rises from the box-shaped body and has a slit for the exit of the dental floss and the perimetral wall rises from the closing body and has—at the end thereof opposite to that of the slit—a fastening portion for a cutting blade.

Moreover, on the planar plate of the box-shaped body there is formed a cut-out in the proximity of a position where a line joining the exit slit with the cutting blade runs.

According to a preferred aspect, a loop or recess is provided on the lateral side of the package, in an area where the line joining the exit slit and the cutting blade runs.

According to another aspect, in the additional body there is obtained a housing for a stock of spool which can be closed by a closing sheet.

According to still another aspect, between the box-shaped body and the closing body there are provided catches/ribbings and mutual engagement recesses which further improve the seal of the interference coupling between box-shaped body and corresponding cover.

BRIEF DESCRIPTION OF THE DRAWINGS

Further features and advantages of the invention are in any case more evident from the following detailed description of some preferred embodiments, given purely by way of a non-limiting example and illustrated in the accompanying drawings, wherein:

FIG. 7 is a view fully similar to that of FIG. 2, but concerning a third variant of the embodiment of the invention; of which

DETAILED DESCRIPTION OF THE PREFERRED EMBODIMENTS

Figures 1, 2:
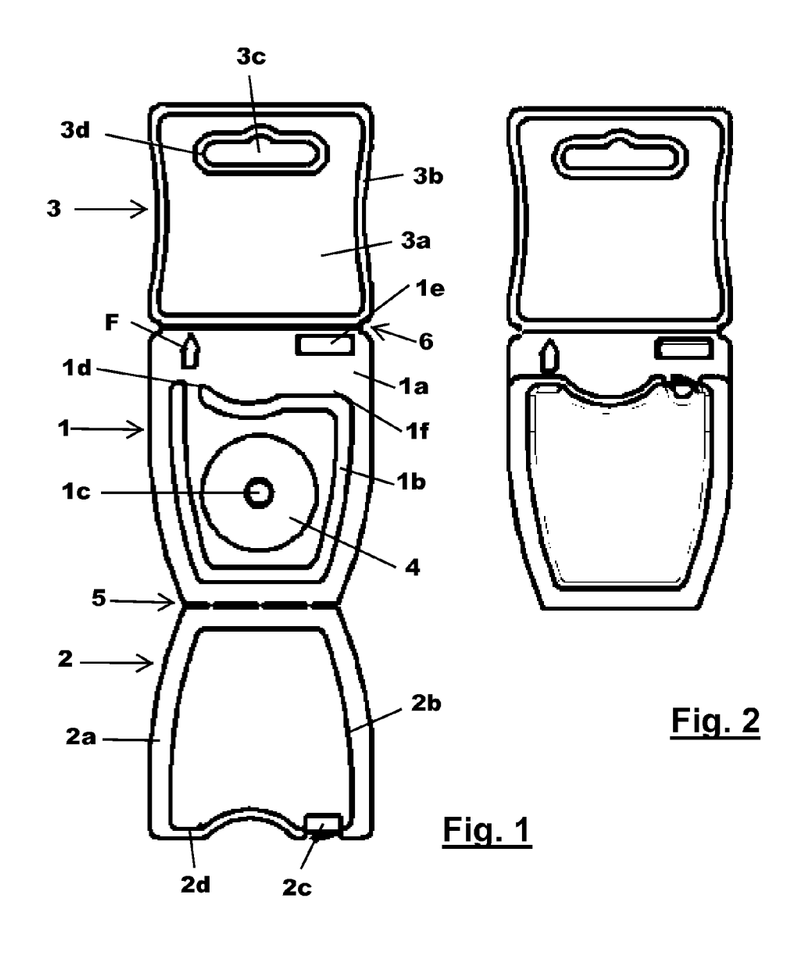
FIG. 1 shows a first embodiment of the package according to the invention in a top plan, spread-out view.
FIG. 2 shows the same package of FIG. 1 in a top plan view, folded to form a box element.

The package according to the invention comprises, according to the embodiment shown in FIGS. 1 and 2, a main body 1 having the function of container, a closing body 2 having the function of cover, and an additional body 3 having the function of suspension means in displays.

Container 1 consists of a planar plate 1a, wherefrom a rib 1b rises perpendicularly, shaped so as to define a substantially closed perimetral contour, which practically determines the side walls of container 1.

In the middle of the space defined by rib 1b, a pin 1c with a pivot function furthermore projects from plate 1a. On this pivot 1c the central axis of a dental floss spool 4 (for example with diameter 31 mm) is intended to be retained, which is housed within container 1.

Rib 1b has at least one interruption, which forms a slit 1d for the exit of the dental floss of spool 4. In the proximity of such interruption, on planar plate 1a an arrow shape F is possibly obtained, intended to show the pulling out direction of the dental floss. Such shape F is in relief.

Moreover, a short protection rib 1e rises from planar plate 1a. It is intended to protect the user's fingers from accidental impacts with a cutting blade lying below, which is shown in the following.

According to a preferred embodiment, on planar plate 1a a cut-out or hole 1g can furthermore be provided, the function of which is disclosed in the following.

With container body 1 there is associated cover body 2; it too consists of a planar plate 2a, wherefrom a cup comes out defined by perimetral walls 2b which follow a line closely similar to the one of rib 1b; unlike said rib, the contour of the perimetral walls 2b of the cup is fully closed and slightly wider than that of rib 1b, to couple externally with said rib, with a forced coupling, to form a closed box element, as better disclosed in the following and as clearly shown in FIGS. 3 and 4.

Figure 2A:
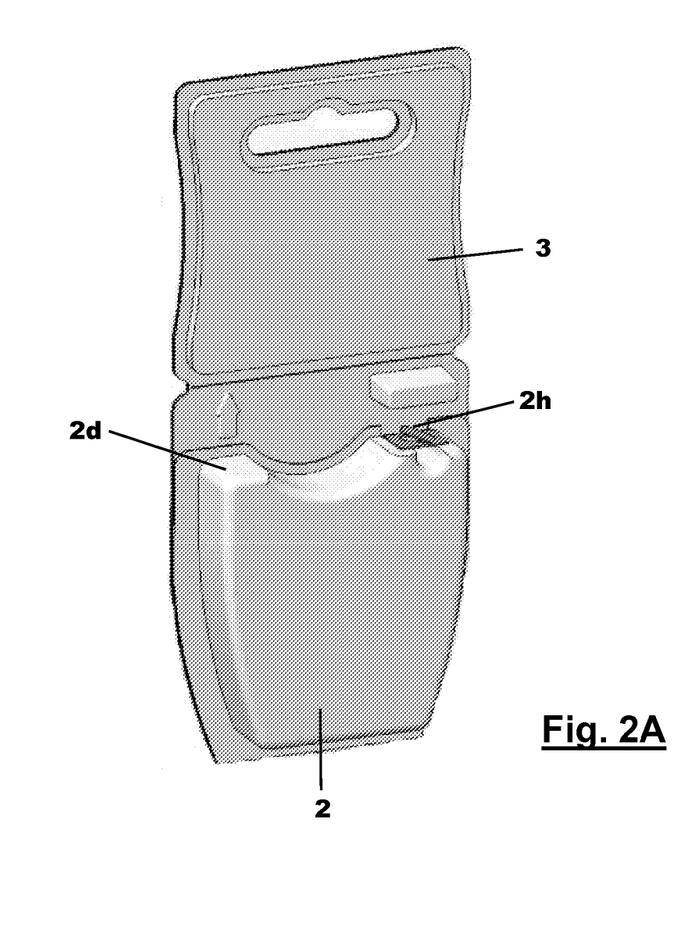
FIG. 2A is similar to FIG. 2 but in a perspective view.
Figure 3:
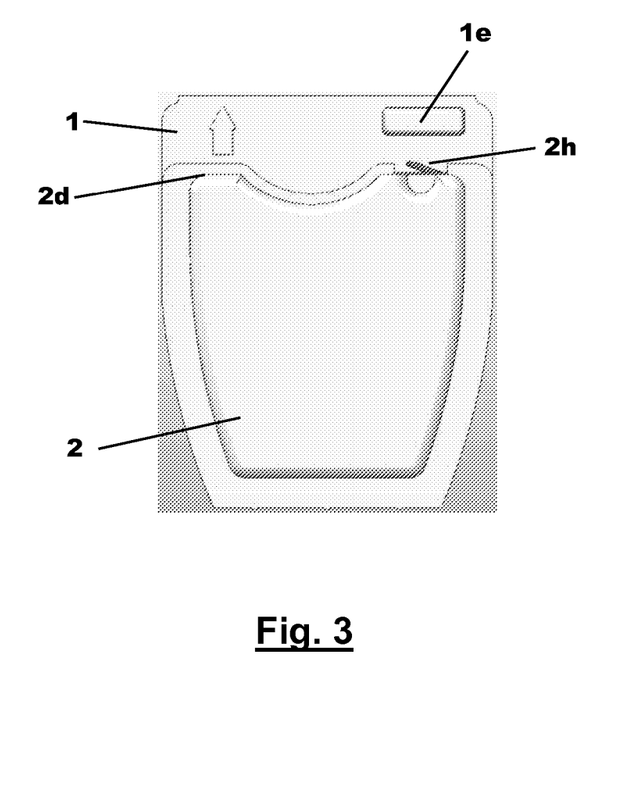
FIG. 3 shows a top plan view of the package of FIG. 2 from which a portion has been cut off.

In correspondence of a corner of the cup of cover 2, perimeter 2b has a fastening portion 2c, whereon a blade or metal cutting nail 2h is applied externally, in the way better shown in FIGS. 2A and 3.

However, in correspondence of an opposite corner, intended to fall adjacent to slit 1d, the cup of cover 2 has a thin slit (not visible in the drawings), through which the dental floss can run.

Additional body 3 is furthermore associated with container body 1—on the side opposite to that of cover 2—which additional body 3 substantially consists of a planar plate 3a, shaped to make it pleasant and possibly perimetrically provided with a thicker stiffening edge 3b.

In a marginal area of body 3—in an area spaced apart from container body 1—an aperture 3c is furthermore formed, which can in turn be provided with a thicker stiffening edge 3d, apt to take up a function of suspension eyelet of the package.

According to the invention, these three bodies 1, 2 and 3 are arranged one after the other in succession on a single piece, mutually separated only by reduced-thickness portions. In particular, between container body 1 and cover body 2 a folding line 5 is provided, intended to facilitate the folding and the overturning by 180° of body 2 on body 1. Between container body 1 and additional body 3, a weakening or tearing-off line 6 is instead provided, for example along which perforations are provided. This weakening line 6 is intended to allow an easy manual detachment of additional body 3 from container 1.

Figure 4:
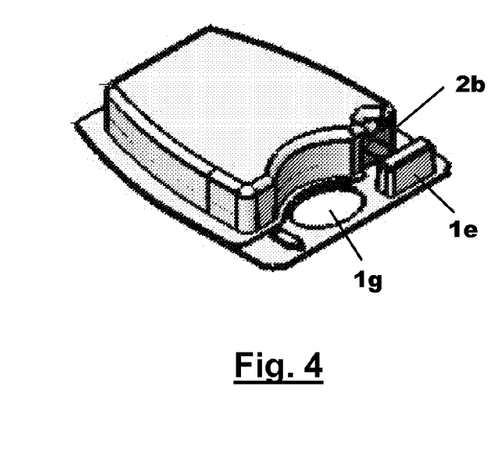
FIG. 4 is a perspective view of an amended embodiment compared to that of FIG. 1.

In actual fact, while body 3 with eyelet 3c is intended to play essentially a package suspension function, for example for the purpose of displaying to the public, body 2 is apt—precisely due to its folding over on body 1—to form said closed box element, to contain spool 4, such as the one illustrated in FIG. 4.

The manufacture of the single piece consisting of three bodies 1, 2 and 3 can occur for example by moulding fully-clear or partly-clear plastic material. In particular, a suitable mould can be provided in which to obtain the device by high-pressure injecting molten plastic material, or it can be provided a mould in which a thermoforming planar plastic plate is introduced, to be heat-deformed.

Figure 5:
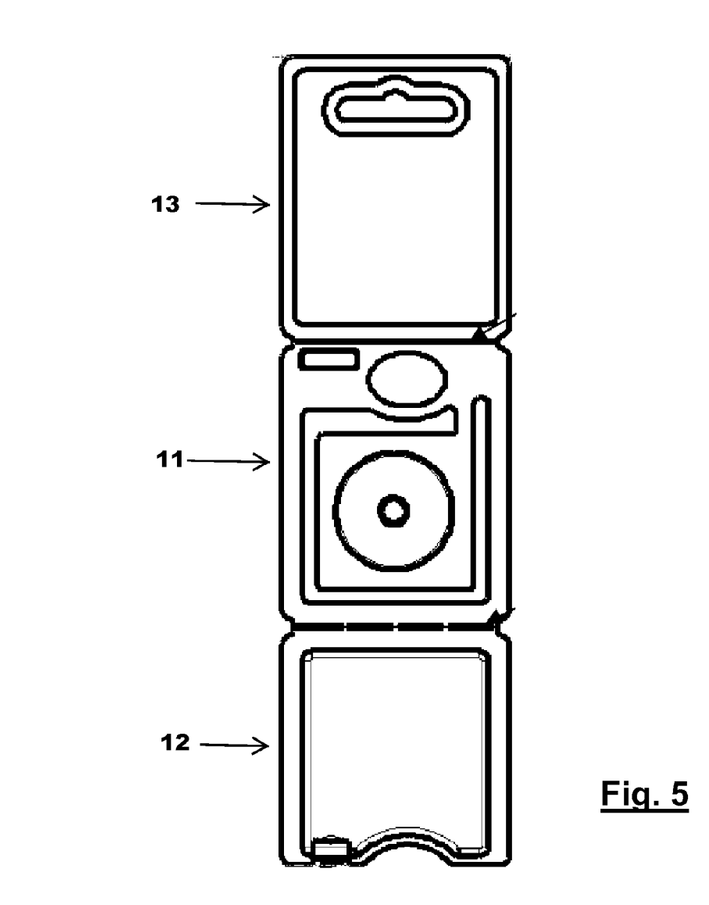
FIGS. 5 and 6 are views fully similar to those of FIGS. 1 and 4, but concerning a second variant of the embodiment of the invention.
Figure 6:
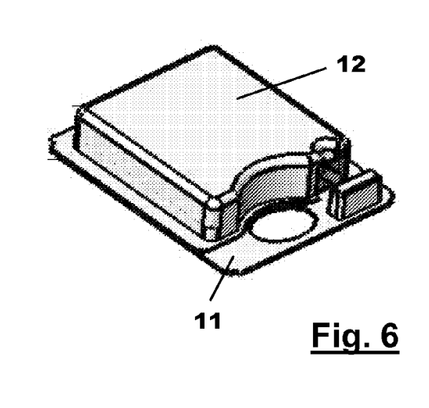
Figure 7:
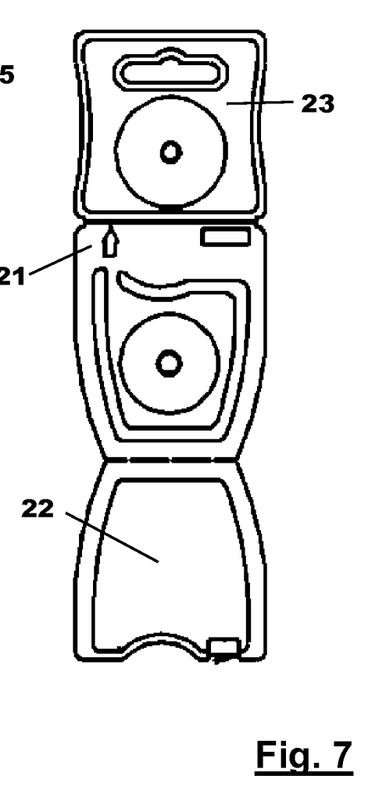
Figure 8:
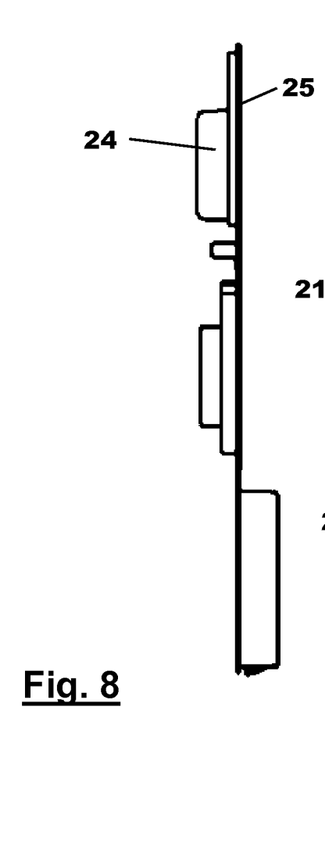
FIGS. 8, 9 and 10 represent an elevation side view and perspective views of two opposite sides, respectively.
Figure 9:
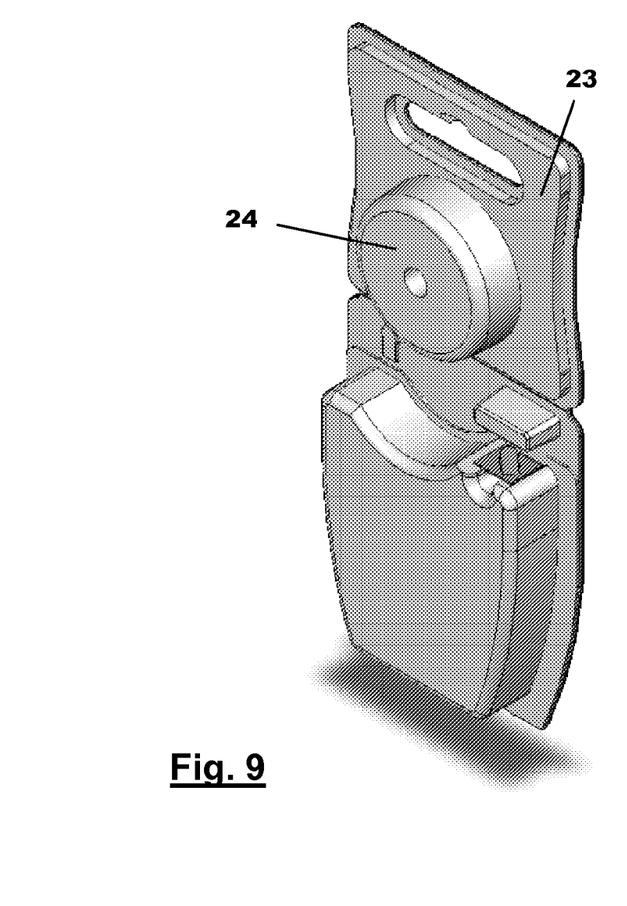
Figure 10:
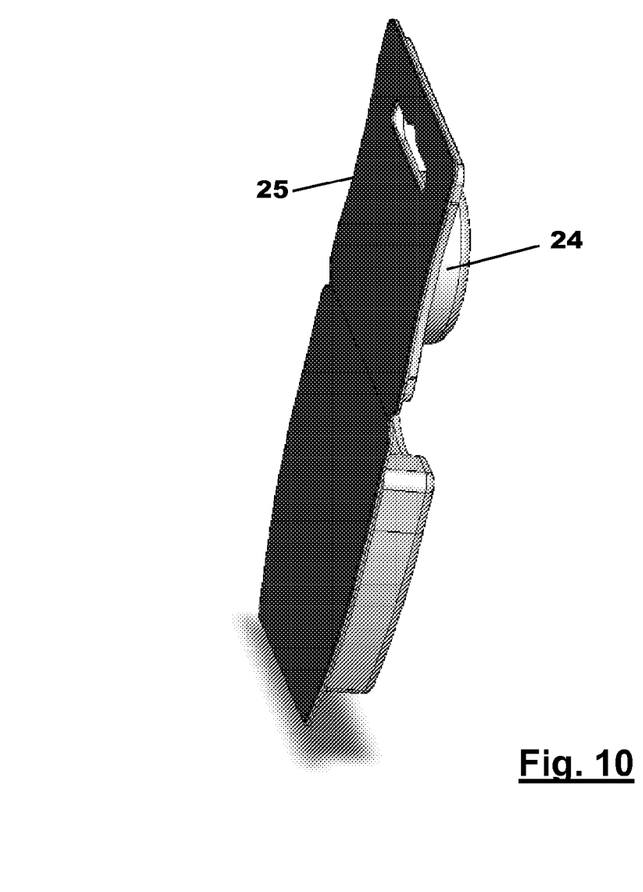
Figure 11:
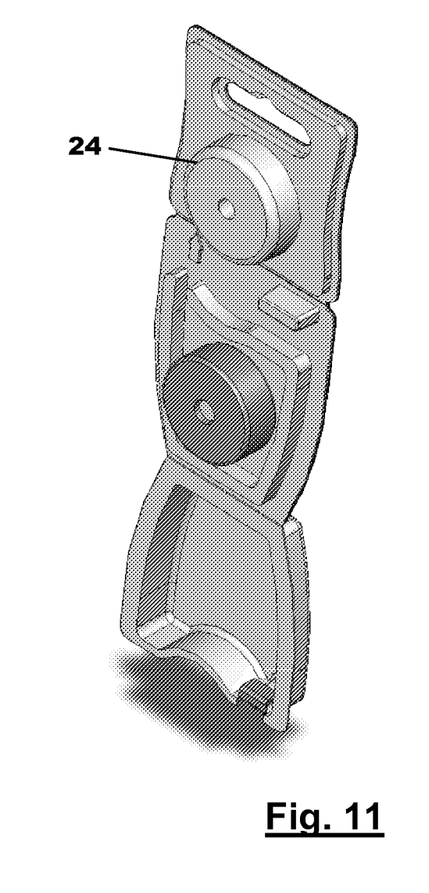
FIG. 11 is a perspective view of the embodiment of FIG. 7 in a spread out condition.

The manufacturing process hence provides a simple moulding of the single piece shown in FIGS. 1, 5 and 11, the subsequent mounting of nail 2h, cutting of exit slit 2d on cup 2, then the introduction of a spool of dental floss and the closure of cover 2 on container body 1.

The container/dispenser is thus ready to be also offered for sale, since it can be hung on the displays through the opening 3c provided on additional body 3.

For a better display to the public, it is provided that the dental floss be partly pulled out from the container and arranged fastened to nail 2h, with a free end portion. This preparation makes the function and the use of the invention container immediately evident to the user. Advantageously, the free end portion of floss is coupled with an adhesive guarantee label, as a further safety measure for the consumer.

The relative sizing of rib 1b and perimeter of cup 2b is such that they couple in close contact with each other, in a substantially dust-proof manner, so that the closure is maintained without the need to add adhesives or other joining materials and that said box element protects the spool perfectly from external agents.

In this coupling of body 2 with body 1, the notched portion 2d of the cup arranges itself opposite slit 1d of body 1, at a short distance therefrom, so as to allow the exit of the floss.

At the same time, fastening portion 2c where cutting blade 2h is supported arranges itself opposite a portion 1f of rib 1b, which is relatively spaced apart from the opposite protection rib 1e, to allow in any case an easy intervention for cutting and cutting off the dental floss during use.

The dental floss typically follows a substantially rectilinear path between notched portion 2d and blade 2h, in which it is firmly retained.

The floss hence comes out of slit 1d and then follows a rectilinear path towards cutting blade 2h: in this portion it remains detached from the lateral wall of cover 2 due to the fact that the cover lateral wall, on this side where the floss comes out, has a loop or recess. Thereby the floss can be easily gripped by fingers to be removed and finally cut off at the desired length.

Hole 1g in planar plate 1a, according to the preferred embodiment, precisely in the proximity of the loop of the cover lateral wall, facilitates the insertion of two fingers astride of the rectilinear floss portion.

In the embodiment of FIGS. 1 to 4, main body 1 and the cover-shaped body 2 thereof have a virtually trapezoidal shape with curved side walls, while suspension body 3 has a rectangular shape with concave side edges.

In the case of the embodiment of FIG. 5 all three bodies 11, 12 and 13 instead have a substantially rectangular shape. For the rest, this embodiment has the same technical features as the embodiment of FIGS. 1 to 4.

Also in the embodiment of FIGS. 7 to 11 the package is of the type having three elements obtained integrally, i.e. comprising a main body 21 and a cover-shaped body 22, forming a box element containing a spool 4 of dental floss, as well as an additional suspension body 23; these three bodies have a contour having a profile identical to that of the embodiment of FIGS. 1 to 4, even though it is easy to think of different profiles.

However, the advantageous feature of this embodiment, over the previous ones, is given by the fact that in additional body 23 a further housing 24 there is formed for a replacement spool of dental floss.

In this case, housing 24 can be closed, after having inserted the replacement spool, by coupling it with a closing sheet 25, consisting for example of a film of paper or metal or plastic material (such as PET or PLA). The coupling of the closing sheet can occur in a conventional way with glues or by hot-joining (should the material be compatible with that of the package). On closing sheet 25 instructions of use or other useful information can be printed.

Figures 12, 13:
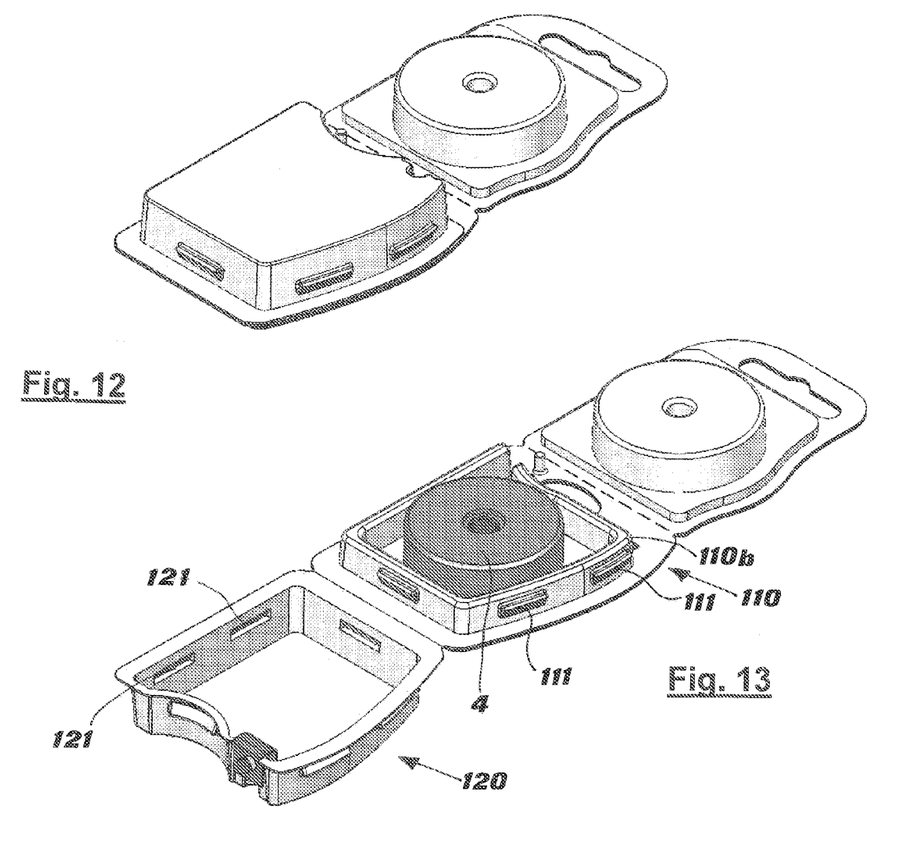
FIGS. 12 and 13 are perspective views of a closed package and of an open package, respectively, according to a variant of the invention

In FIGS. 12 and 13 a further embodiment is shown, which, mostly, is equivalent to those already described. In this case, in order to obtain a firmer and safer coupling of main body 110 with cover 120, along lateral wall 110b, catches or ribbings 111 are obtained on the outer surface, intended to couple with corresponding grooves or recesses 121 obtained on the lateral contour of the cup of cover 120. As shown, catches 111 and corresponding recesses 121 are evenly arranged along the coupling surfaces of the main body and the cover; for example there are two on each of the side walls and one on the wall opposite the floss exit wall.

As can be inferred from the above reported description, the objects set forth in the premises are perfectly achieved.

As a matter of fact, by the teaching of the invention it is possible to manufacture a single-piece dental floss container/dispenser which hence does not require significant assembling operations already arranged also for sales display, which exonerates from the need to provide a further package, positively affecting costs and the environmental impact. Package assembly requires no use of adhesives or other joining systems and can hence occur directly on the package line where loading of floss spools occurs.

However, it is understood that the invention must not be considered limited to the particular, above-illustrated arrangements, which represent some exemplifying embodiments thereof, but that a number of variants are possible, all within the reach of a person skilled in the field, without departing from the scope of protection of the invention, as defined in the following claims.

For example, by using suitable moulding techniques, it is possible to manufacture the package with a material other than plastics, such as thin metal.

The invention claimed is:

1. Dental floss package, of the type comprising a box-shaped body, wherein the dental floss is to be housed in the shape of a spool, further comprising a cutting blade and a closing body, as well as an additional body (3, 23) provided with an aperture (3c) for fastening the same to a display, characterised in that
    said additional body is integrally obtained with said box-shaped body or said closing body but detachable along a weakening line (6), and in that
    said box-shaped body (1, 11, 21, 110) and said closing body (2, 12, 22, 120) are also obtained integrally and joined along a thin folding line (5), and in that
    said box-shaped body (1, 11, 21, 110) is interference-coupled with said closing body (2, 12, 22, 120) by means of a wall which encircles said spool (4).

2. Package as claimed in claim 1, characterised in that said closing body (2, 12, 22, 120), overturned by 180° about said thin folding line (5), is coupled with said box-shaped body (1) to form a housing which encloses the dental floss spool (4).

3. Package as claimed in claim 2, wherein said box-shaped body (1, 21) and said closing body (2, 22) substantially consist of a planar plate (1a, 2a), wherefrom ribbings and perimetral walls (1b, 2b) project perpendicularly, apt to interference-couple with one another to form said housing.

4. Package as claimed in claim 3, wherein said closing body (2, 12, 22, 120) is cup-shaped.

5. Dental floss package as claimed in claim 3, wherein said ribbing (1b) rises from said box-shaped body (1) and has a slit (1d) for the exit of the dental floss and the perimetral wall (2a) rises from the closing body (2) and has, at the end thereof opposite to the end of the slit (1d), a fastening portion (2c) for a cutting blade (2h).

6. Dental floss package as claimed in claim 5, wherein on said planar plate (1a) of the box-shaped body there is formed a cut-out (1g) in the proximity of a position where a line joining said exit slit (1d) and said cutting blade (2h) runs.

7. Dental floss package as claimed in claim 5, wherein on the lateral wall of said package, in the area affected by the line joining said exit slit (1d) and said cutting blade (2h), a loop or recess is provided.

8. Dental floss package as claimed in claim 1, wherein in the additional body (23) a housing (24) is provided for a storage spool, which can be closed by a closing sheet (25).

9. Dental floss package as claimed in claim 1, wherein said box-shaped body (1, 21), said closing body (2, 22) and said additional body (3, 23) are all obtained integrally.

10. Dental floss package as claimed in claim 1, wherein between said box-shaped body (1, 11, 21, 110) and said closing body (2, 12, 22, 120) catches (111) and recesses (121) for mutual engagement are provided.

11. Dental floss package, of the type comprising a box-shaped body obtained by moulding, wherein the dental floss can be housed in the form of a spool, further comprising a cutting blade and a closing body,
    characterised in that said box-shaped body (1, 11, 21, 110) and said closing body (2, 12, 22, 120) are obtained integrally and joined along a thin folding line (5), an additional body (3, 23) equipped with an aperture (3c) for the fastening thereof to a display being further provided, and in that
    said box-shaped body (1, 11, 21, 110) is interference-coupled with said closing body (2, 12, 22, 120) by means of a wall encircling said spool (4).

12. Package as claimed in claim 11, wherein said additional body (3, 23) provided with an aperture (3c) is obtained integrally with said box-shaped body or said closing body but detachable along a weakening line (6).

13. Package as claimed in claim 11, characterised in that said closing body (2, 12, 22, 120), overturned by 180° about said thin folding line (5), is coupled with said box-shaped body (1) to form a housing which encloses the dental floss spool (4).

14. Dental floss package as claimed in claim 11, wherein in the additional body (23) a housing (24) is provided for a storage spool, which can be closed by a closing sheet (25).

15. Dental floss package as claimed in claim 11, wherein said box-shaped body (1, 21), said closing body (2, 22) and said additional body (3, 23) are all obtained integrally.

16. Dental floss package as claimed in claim 11, wherein between said box-shaped body (1, 11, 21, 110) and said closing body (2, 12, 22, 120) catches (111) and recesses (121) for mutual engagement are provided.

17. Package as claimed in claim 13, wherein said box-shaped body (1, 21) and said closing body (2, 22) substantially consist of a planar plate (1a, 2a), wherefrom ribbings and perimetral walls (1b, 2b) project perpendicularly, apt to interference-couple with one another to form said housing.

18. Package as claimed in claim 14, wherein said closing body (2, 12, 22, 120) is cup-shaped.

19. Dental floss package as claimed in claim 15, wherein said ribbing (1b) rises from said box-shaped body (1) and has a slit (1d) for the exit of the dental floss and the perimetral wall (2a) rises from the closing body (2) and has, at the end thereof opposite to the end of the slit (1d), a fastening portion (2c) for a cutting blade (2h).

20. Dental floss package as claimed in claim 16, wherein on said planar plate (1a) of the box-shaped body there is formed a cut-out (1g) in the proximity of a position where a line joining said exit slit (1d) and said cutting blade (2h) runs.

21. Dental floss package as claimed in claim 16, wherein on the lateral wall of said package, in the area affected by the line joining said exit slit (1d) and said cutting blade (2h), a loop or recess is provided.

\* \* \* \* \*